United States Patent
Burri et al.

(10) Patent No.: US 7,371,762 B2
(45) Date of Patent: May 13, 2008

(54) 3-SUBSTITUTED 6,7-DIHYDROXYTETRA-HYDROISOQUINOLINE DERIVATIVES FOR USE AS ANTIBACTERIAL AGENTS

(75) Inventors: Kaspar Burri, Binningen (CH); Laurent Schmitt, Sierentz (FR); Khalid Islam, Reinach (CH)

(73) Assignee: Arpida AG (CH)

( * ) Notice: Subject to any disclaimer, the term of this patent is extended or adjusted under 35 U.S.C. 154(b) by 503 days.

(21) Appl. No.: 10/487,877

(22) PCT Filed: Aug. 9, 2002

(86) PCT No.: PCT/EP02/08916

§ 371 (c)(1),
(2), (4) Date: Aug. 18, 2004

(87) PCT Pub. No.: WO03/018017

PCT Pub. Date: Mar. 6, 2003

(65) Prior Publication Data

US 2004/0266817 A1  Dec. 30, 2004

(30) Foreign Application Priority Data

Aug. 27, 2001  (EP)  .................. PCT/EP01/09846

(51) Int. Cl.
*C07D 217/12*  (2006.01)
*A61K 31/47*  (2006.01)
(52) U.S. Cl. ...................... 514/310; 546/146
(58) Field of Classification Search ............... 514/310; 546/146
See application file for complete search history.

(56) References Cited

U.S. PATENT DOCUMENTS 5,124,337 A   6/1992  Dugar et al.

FOREIGN PATENT DOCUMENTS

| CS | 8207825 | 6/1983 |
| FR | 2662940 | * 12/1991 |
| GB | 1 475 913 | 6/1977 |

OTHER PUBLICATIONS

Spangler et al., J. Org. Chem., vol. 39, pp. 1368-1374 (1974).
Vicario et al., J. Org. Chem., vol. 64, pp. 4610-4616 (1999).
Dominguez et al., Tetrahedron, vol. 44, pp. 203-208 (1988).
Yokoyama et al., J. Org. Chem., vol. 64, pp. 611-617 (1999).
Kim et al., Bioorganic & Medicinal Chemistry Letters 9, pp. 85-90 (1999).
Cox et al., Chemical Reviews, vol. 95, pp. 1797-1842 (1995).
O'Reilly et al., "Optically Pure (S)-6,7-Dimethoxy-1,2,3,4-Tetrahydro-3-Isoquinolinecarboxylic Acid and Asymmetric Hydrogenation Studies Related to Its Preparation", Papers, pp. 550-556, Occidental Chemical Corporation, Technology Center, 2801 Long Road, Grand Island, NY 14072, U.S.A. (Jul. 1990).
Cope et al., "The Rearrangement of Allyl Groups in Three-carbon Systems. VI. Benzene and Phenanthrene Derivatives", Departments of Chemistry of Bryn Mawr College and The Massachusetts Institute of Technology, U.S.A. vol. 78, pp. 2547-2551 (Jun. 5, 1956).
Organic Syntheses, Collective vol. 2, pp. 55-56 (Sixth Printing, Oct. 1950).
Valenta, Vladimir et al.; "Alpha-(4-TOLYL) Dopamine Derivatives"; Collection of Czechoslovak Chemical Communications, Academic Press, London, Great Britain, vol. 48, No. 5, 1983, pp. 1447-1463.

* cited by examiner

*Primary Examiner*—Zinna N. Davis
(74) *Attorney, Agent, or Firm*—Dickstein, Shapiro, LLP.

(57) ABSTRACT

The invention relates to novel tetrahydroisoquinoline derivatives of general formula I and theirs use as active ingredients in the preparation of pharmaceutical compositions. The invention also concerns related aspects including processes for the preparation of the compounds, pharmaceutical compositions containing one or more of those compounds and their use as anti-infectives, wherein $R^1$, $R^2$ and $R^3$ are as defined in claim 1.

10 Claims, No Drawings

3-SUBSTITUTED 6,7-DIHYDROXYTETRA-HYDROISOQUINOLINE DERIVATIVES FOR USE AS ANTIBACTERIAL AGENTS

The present invention relates to novel tetrahydroisoquinolines of the general formula 1, to a process for the manufacture of these tetrahydroisoquinolines, to pharmaceutical compositions containing them and to their use in the treatment of microbial infections.

Related tetrahydroisoquinolines have been investigated previously. Specifically, for compounds of general formula 1 ($R^3$=4-tolyl) CNS-activity in vivo and antimicrobial activity in vitro has been claimed by Vladimir Valenta et al. in Czech Patent Application No. CS 82-7825 (1982). Other related structures can be found in: "Preparation of N-acyltetrahydroisoquinolines as inhibitors of acyl-coenzyme A: cholesterol acyltransferase", Sundeep Dugar and Timothy Kogan; U.S. patent application No U.S. Pat. No. 5,124,337 (1992).

It has been found that compounds of the general formula 1 exhibit antibacterial activity and consequently are generally useful to combat bacterial pathogens in human and animals, e.g. to combat Gram positive pathogens such as *Staphylococcus aureus*, *Staphylococcus epidermidis*, *Enterococcus faecalis* or *Streptococcus pneumoniae* etc., and Gram negatives like *Haemophilus influenzae*, *Escherichia coli*, *Klebsiella pneumoniae* or *Proteus vulgaris*.

Minimal inhibitory concentrations (MIC) were determined in accordance with the National Committee for Clinical Laboratory Standards (NCCLS) procedure [M7-A5, 2001].

The results obtained are summarized in table 1 and are expressed in jig/ml. In this table 1, EC 25922 means *Escherichia coli* ATCC25922, EC DC2 means *Escherichia coli* DC2, SA 25923 means *Staphylococcus aureus* ATCC25923 and SA 101 means *Staphylococcus aureus* 101. (ATCC=American Type Culture Collection)

M7-A5* (2001): Methods for Dilution Antimicrobial Susceptibility Tests for Bacteria that Grow Aerobically; Approved Standard—Fifth Edition American National Standard.

TABLE 1

| Example | IUPAC name | EC 25922 | EC DC2 | SA 25923 | SA 101 |
|---|---|---|---|---|---|
| 1 | 3-(4-Phenoxy-phenyl)-1,2,3,4-tetrahydro-isoquinoline-6,7-diol | 32 | 8 | 8 | 8 |
| 2 | 2-Benzyl-3-(4-phenoxy-phenyl)-1,2,3,4-tetrahydro-isoquinoline-6,7-diol | >128 | 64 | 64 | 32 |
| 3 | 1-Methyl-3-(4-phenoxy-phenyl)-1,2,3,4-tetrahydro-isoquinoline-6,7-diol | | 32 | 16 | |
| 4 | 3-(4-Methoxy-naphthalen-1-yl)-1,2,3,4-tetrahydro-isoquinoline-6,7-diol | | 32 | 32 | |
| 5 | 3-(4-Hydroxy-naphthalen-1-yl)-1,2,3,4-tetrahydro-isoquinoline-6,7-diol | | 16 | 32 | |
| 6 | 3-Hydroxymethyl-1,2,3,4-tetrahydro-isoquinoline-6,7-diol | 64 | 32 | 16 | 16 |
| 7 | 3-Dibenzofuran-2-yl-1,2,3,4-tetrahydro-isoquinoline-6,7-diol | 64 | 32 | 8 | 16 |
| 8 | 3-(4-Phenylsulfanyl-phenyl)-1,2,3,4-tetrahydro-isoquinoline-6,7-diol | 64 | 32 | 8 | 32 |
| 9 | 3-(2,4-Dichloro-phenyl)-1,2,3,4-tetrahydro-isoquinoline-6,7-diol | 128 | 64 | 64 | 64 |
| 10 | 3-(2,4-Dichloro-phenoxymethyl)-1,2,3,4-tetrahydro-isoquinoline-6,7-diol | 128 | 2 | 8 | 16 |
| 11 | 2-Benzyl-3-(2,4-dichloro-phenoxymethyl)-1,2,3,4-tetrahydro-isoquinoline-6,7-diol | >128 | >128 | 8 | 8 |
| 12 | 3-Biphenyl-4-yl-1,2,3,4-tetrahydro-isoquinoline-6,7-diol | 16 | 8 | 4 | 16 |
| 13 | 3-(3,4-Dichloro-phenoxymethyl)-1,2,3,4-tetrahydro-isoquinoline-6,7-diol | >128 | 16 | 16 | 16 |
| 14 | 3-(2,5-Dichloro-phenoxymethyl)-1,2,3,4-tetrahydro-isoquinoline-6,7-diol | 128 | 32 | 64 | 64 |
| 15 | 3-(4-Chloro-phenyl)-1,2,3,4-tetrahydro-isoquinoline-6,7-diol | 128 | 32 | 16 | 32 |
| 16 | 3-(4-Bromo-phenyl)-1,2,3,4-tetrahydro-isoquinoline-6,7-diol | >128 | 32 | 8 | 64 |
| 17 | 3-(4'-Trifluoromethyl-biphenyl-4-yl)-1,2,3,4-tetrahydro-isoquinoline-6,7-diol | 64 | 8 | 4 | 8 |
| 18 | 3-(4'-Dimethylamino-biphenyl-4-yl)-1,2,3,4-tetrahydro-isoquinoline-6,7-diol | >128 | 8 | 4 | 16 |
| 19 | 3-(4'-Hydroxy-biphenyl-4-yl)-1,2,3,4-tetrahydro-isoquinoline-6,7-diol | >128 | 64 | 128 | 128 |
| 20 | 3-(2'-Hydroxy-biphenyl-4-yl)-1,2,3,4-tetrahydro-isoquinoline-6,7-diol | 128 | 32 | 16 | 32 |
| 21 | 3-(2',4'-Difluoro-biphenyl-4-yl)-1,2,3,4-tetrahydro-isoquinoline-6,7-diol | 32 | 8 | 8 | 8 |
| 22 | 4'-(6,7-Dihydroxy-1,2,3,4-tetrahydro-isoquinolin-3-yl)-biphenyl-3-carbonitrile | >128 | 64 | 128 | >128 |

The present invention relates to novel tetrahydroisoquinolines of the general formula 1:

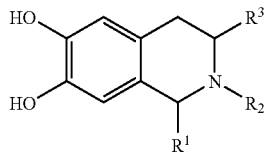

wherein
R¹ represents hydrogen or lower alkyl,
R² represents hydrogen; aryl; aryl-lower alkyl; heteroaryl; heteroaryl-lower alkyl; whereby the aryl and heteroaryl residues may be mono-, di- or tri-substituted with lower alkyl, hydroxy, lower alkoxy, halogen, trifluoromethyl, amino, lower alkylamino, lower alkylendioxy and which substituents may be the same or different,
R³ represents one of the groups: —(CH$_2$)$_m$—O—(CH$_2$)$_n$—Ar¹; —(CH$_2$)$_m$—NH—(CH$_2$)$_n$—Ar¹; —(CH$_2$)$_m$—S—(CH$_2$)$_n$—Ar¹; —(CH=CH)—(CH$_2$)$_n$—Ar¹; —CHOH—(CH$_2$)$_n$—Ar¹; —(CH$_2$)$_n$—Ar²; —(CH$_2$)$_n$—Ar³; —(CH$_2$)$_n$—Ar⁴ whereby in these groups
m represents the number 1, 2 and 3;
n represents the number 0, 1, 2 and 3;
Ar¹ represents hydrogen; an aryl or heteroaryl group which groups may be unsubstituted or mono-, di-, or trisubstituted with a substituent independently selected from the group D, whereby D represents hydroxy, lower alkyl, lower alkoxy, lower alkylendioxy, aryl, aryloxy, lower alkyl-sulfanyl, arylsulfanyl, halogen, amino, lower alkylamino, lower di-alkylamino, trifluoromethyl;
Ar² represents an aryl or heteroaryl group which groups are di-, or trisubstituted with a substituent selected from the group D, whereby D is as defined above;
Ar³ represents an aryl or heteroaryl group which groups are monosubstituted with aryl, aryloxy, arylsulfanyl, lower alkyl-sulfanyl, trifluoromethyl, lower alkylendioxy;
Ar⁴ represents an aryl or heteroaryl group which groups are monosubstituted with
Ar¹ with the proviso that Ar¹ does not represent hydrogen;

and pure enantiomers, mixture of enantiomers, pure diastereomers, mixture of diastereomers, diastereomeric racemates and stereoisomers and pharmaceutically acceptable salts thereof.

Preferred compounds are compounds of the general formula 2,

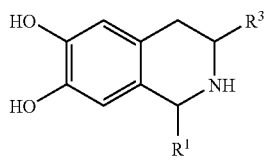

wherein
R¹ and R³ have the meaning given in the general formula 1 above;
and pure enantiomers, mixture of enantiomers, pure diastereomers, mixture of diastereomers, diastereomeric racemates and stereoisomers and pharmaceutically acceptable salts thereof.

Very preferred compounds are those of the general formula 1, wherein R¹ represents hydrogen.
Especially preferred compounds are:
1-(2,4-Dichloro-phenyl)-1,2,3,4-tetrahydro-isoquinoline-6,7-diol;
1-(2,4-Dichloro-benzyl)-1,2,3,4-tetrahydro-isoquinoline-6,7-diol;
1-(4-Chloro-benzyl)-1,2,3,4-tetrahydro-isoquinoline-6,7-diol;
1-Cyclopropyl-3-(4-phenoxy-phenyl)-1,2,3,4-tetrahydro-isoquinoline-6,7-diol;
1-Cyclopropyl-3-dibenzofuran-2-yl-1,2,3,4-tetrahydro-isoquinoline-6,7-diol;
1-Cyclopropyl-3-(4-phenylsulfanyl-phenyl)-1,2,3,4-tetrahydro-isoquinoline-6,7-diol;
3-(4-methylsulfanyl-phenyl)-1,2,3,4-tetrahydro-isoquinoline-6,7-diol;
2-(2,4-Dichloro-benzyl)-3-(4-methylsulfanyl-phenyl)-1,2,3,4-tetrahydro-isoquinoline-6,7-diol;
3-(4-Methoxy-phenyl)-1,2,3,4-tetrahydro-isoquinoline-6,7-diol;
3-(4-Hydroxy-phenyl)-1,2,3,4-tetrahydro-isoquinoline-6,7-diol;
1-Cyclopropyl-3-(4-hydroxy-phenyl)-1,2,3,4-tetrahydro-isoquinoline-6,7-diol;
3-(2,4-Dichloro-benzyl)-1,2,3,4-tetrahydro-isoquinoline-6,7-diol;
2-Benzyl-3-phenoxymethyl-1,2,3,4-tetrahydro-isoquinoline-6,7-diol;
3-Phenoxymethyl-1,2,3,4-tetrahydro-isoquinoline-6,7-diol;
2-Benzyl-3-(4-chloro-phenoxymethyl)-1,2,3,4-tetrahydro-isoquinoline-6,7-diol;
3-(4-Chloro-phenoxymethyl)-1,2,3,4-tetrahydro-isoquinoline-6,7-diol;
2-Benzyl-3-(2-chloro-phenoxymethyl)-1,2,3,4-tetrahydro-isoquinoline-6,7-diol;
3-(2-Chloro-phenoxymethyl)-1,2,3,4-tetrahydro-isoquinoline-6,7-diol;
2-Benzyl-3-(2,5-dichloro-phenoxymethyl)-1,2,3,4-tetrahydro-isoquinoline-6,7-diol;
3-(2,5-Dichloro-phenoxymethyl)-1,2,3,4-tetrahydro-isoquinoline-6,7-diol;
2-Benzyl-3-(4-nitro-phenoxymethyl)-1,2,3,4-tetrahydro-isoquinoline-6,7-diol;
3-(4-Amino-phenoxymethyl)-1,2,3,4-tetrahydroiso-quinoline-6,7-diol;
2-Benzyl-3-(2-nitro-phenoxymethyl)-1,2,3,4-tetrahydro-isoquinoline-6,7-diol;
3-(2-Amino-phenoxymethyl)-1, 2,3,4-tetrahydro-isoquinoline-6,7-diol;
2-Benzyl-3-(2-methoxy-ethoxymethyl)-1,2,3,4-tetrahydro-isoquinoline-6,7-diol;
3-(2-Methoxy-ethoxymethyl))-1,2,3,4-tetrahydro-isoquinoline-6,7-diol;
2-Benzyl-3-hexyloxymethyl-1,2,3,4-tetrahydro-isoquinoline-6,7-diol;
3-Pentyloxymethyl-1,2,3,4-tetrahydro-isoquinoline-6,7-diol;
2-Benzyl-3-[(2-pyridin-2-yl-ethylaminoymethyl]-1,2,3,4-tetrahydro-isoquinoline-6,7-diol;
2-Benzyl-3-(hydroxy-p-tolyl-methyl)-1,2,3,4-tetrahydro-isoquinoline-6,7-diol;
3-(Hydroxy-p-tolyl-methyl)-1,2,3,4-tetrahydro-isoquinoline-6,7-diol;
3-(4-Methyl-benzyl)-1,2,3,4-tetrahydro-isoquinoline-6,7-diol;
2-Benzyl-3-styryl-1,2,3,4-tetrahydro-isoquinoline-6,7-diol;

3-Phenethyl-1,2,3,4-tetrahydro-isoquinoline-6,7-diol.

Most preferred compounds are:

3-(4-Phenoxy-phenyl)-1,2,3,4-tetrahydro-isoquinoline-6,7-diol;
2-Benzyl-3-(4-phenoxy-phenyl)-1,2,3,4-tetrahydro-isoquinoline-6,7-diol;
1-Methyl-3-(4-phenoxy-phenyl)-1,2,3,4-tetrahydro-isoquinoline-6,7-diol;
3-(4-Methoxy-naphthalen-1-yl)-1,2,3,4-tetrahydro-isoquinoline-6,7-diol;
3-(4-Hydroxy-naphthalen-1-yl)-1,2,3,4-tetrahydro-isoquinoline-6,7-diol;
3-Hydroxymethyl-1,2,3,4-tetrahydro-isoquinoline-6,7-diol;
3-Dibenzofuran-2-yl-1, 2,3,4-tetrahydro-isoquinoline-6,7-diol;
3-(4-Phenylsulfanyl-phenyl)-1,2,3,4-tetrahydro-isoquinoline-6,7-diol;
3-(2,4-Dichloro-phenyl)-1,2,3,4-tetrahydro-isoquinoline-6,7-diol;
3-(2,4-Dichloro-phenoxymethyl)-1,2,3,4-tetrahydro-isoquinoline-6,7-diol;
2-Benzyl-3-(2,4-dichloro-phenoxymethyl)-1,2,3,4-tetrahydro-isoquinoline-6,7-diol;
3-Biphenyl-4-yl-1,2,3,4-tetrahydro-isoquinoline-6,7-diol;
3-(3,4-Dichloro-phenoxymethyl)-1,2,3,4-tetrahydro-isoquinoline-6,7-diol;
3-(2,5-Dichloro-phenoxymethyl)-1,2,3,4-tetrahydro-isoquinoline-6,7-diol;
3-(4-Chloro-phenyl)-1,2,3,4-tetrahydro-isoquinoline-6,7-diol;
3-(4-Bromo-phenyl)-1,2,3,4-etrahydro-isoquinoline-6,7-diol;
3-(4'-Trifluoromethyl-biphenyl-4-yl)-1,2,3,4-tetrahydro-isoquinoline-6,7-diol;
3-(4'-Dimethylamino-biphenyl-4-yl)-1,2,3,4-tetrahydro-isoquinoline-6,7-diol;
3-(4'-Hydroxy-biphenyl-4-yl)-1,2,3,4-tetrahydro-isoquinoline-6,7-diol;
3-(2'-Hydroxy-biphenyl-4-yl)-1,2,3,4-tetrahydro-isoquinoline-6,7-diol;
3-(2',4'-Difluoro-biphenyl-4-yl)-1,2,3,4-tetrahydro-isoquinoline-6,7-diol;
4'-(6,7-Dihydroxy-1,2,3,4-tetrahydro-isoquinolin-3-yl)-biphenyl-3-carbonitrile;

In the definitions of the general formula 1—if not otherwise stated—the expression lower means straight and branched chain groups with one to seven carbon atoms, preferably 1 to 4 carbon atoms. Examples of lower alkyl and lower alkoxy groups are methyl, ethyl, n-propyl, isopropyl, cyclopropyl, n-butyl, isobutyl, sec.-butyl, tert.-butyl, pentyl, hexyl, heptyl, methoxy, ethoxy, propoxy, butoxy, iso-butoxy, sec.-butoxy and tert.-butoxy. The expression heteroaryl means six-membered aromatic rings containing one to four nitrogen atoms, mono- or dibenzofused six-membered aromatic rings containing one to three nitrogen atoms, five-membered aromatic rings containing one oxygen or one nitrogen or one sulfur atom, mono- or dibenzo-fused five-membered aromatic rings containing one oxygen or one nitrogen or one sulfur atom, five membered aromatic rings containing an oxygen and nitrogen atom and benzo fused derivatives thereof, five-membered aromatic rings containing a sulfur and a nitrogen atom and benzo fused derivatives thereof, five-membered aromatic rings containing two nitrogen atoms and benzo fused derivatives thereof, five membered aromatic rings containing three nitrogen atoms and benzo fused derivatives thereof or the tetrazolyl ring; e.g. furanyl, thienyl, pyrrolyl, pyridinyl, pyrimidinyl, indolyl, quinolinyl, isoquinolinyl, imidazolyl, triazinyl, thiazinyl, thiazolyl, isothiazolyl, pyridazinyl, oxazolyl, isoxazolyl, triazinyl, thiazinyl, thiazolyl, isothiazolyl, pyridazinyl, oxazolyl, isoxazolyl etc. whereby such rings may be substituted with lower alkyl, amino, lower alkylamino, lower di-alkylamino, halogen, hydroxy, lower alkoxy, trifluoromethyl, or another heteroaryl-(preferrably tetrazolyl) or heterocyclyl-ring (preferrably 5-oxo-1,2,4-oxadiazolyl, 5-oxo-1,2,4-triazolyl, 5-oxo-1,2,4-thiadiazolyl, 5-thioxo-1,2,4-oxadiazolyl or 2-oxo-1,2,3,5-oxathiadiazolyl). The expression aryl represents unsubstituted as well as mono-, di- or tri-substituted aromatic rings with 6 to 10 carbon atoms like phenyl or naphtyl rings which may be substituted with halogen, hydroxy, lower alkyl, lower alkoxy, lower alkyl-sulfanyl, arylsulfanyl, amino, lower alkylamino, lower di-alkylamino, trifluoromethyl, or lower alkylendioxy forming with the phenyl ring a five- or six-membered ring.

However, in the case of $Ar^2$, aryl represents di- or trisubstituted aryl or heteroaryl groups.

The expression pharmaceutically acceptable salts encompasses either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methane sulfonic acid, p-toluene sulfonic acid and the like or in case the compound of formula 1 and 2 is acidic in nature with an inorganic base like an alkali or earth alkali base, e.g. sodium hydroxide, potassium hydroxide, calcium hydroxide etc.

Because of their ability to inhibit Gram positive and Gram negative bacteria, the described compounds can be used for the treatment of diseases which are associated with an infection by such type of pathogens. They are valuable anti-infectives.

The compounds can be administered orally, rectally, parenterally, e.g. by intravenous, intramuscular, subcutaneous, intrathecal or transdermal administration or sublingually or as ophthalmic preparation or administered as aerosol. Examples of applications are capsules, tablets, orally administered suspensions or solutions, suppositories, injections, eye-drops, ointments or aerosols/nebulizers.

Preferred applications are intravenous, intramuscular, or oral administrations as well as eye drops. The dosage used depends upon the type of the specific active ingredient, the age and the requirements of the patient and the kind of application. Generally, dosages of 0.1-50 mg/kg body weight per day are considered. The preparations with compounds of formulae 1 and 2 can contain inert or as well pharmacodynamically active excipients like sulphonamides. Tablets or granules, for example, could contain a number of binding agents, filling excipients, carrier substances or diluents.

These compositions may be administered in enteral or oral form e.g. as tablets, dragees, gelatine capsules, emulsions, solutions or suspensions, in nasal form like sprays or rectally in form of suppositories. These compounds may also be parenterally administered as an intramuscular or intravenous form, e.g. in form of injectable solutions.

These pharmaceutical compositions may contain the compounds of general formula 1 and 2 as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols etc. may be used. For the preparation of solutions and syrups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, anti oxidants etc.

The compounds of general formula 1 and 2 may also be used in co-therapy with one or more other therapeutically used classes of antimicrobial substances, for example, beta-lactams e.g. penicillins and cephalosporins; glycopeptides; quinolones; tetracyclines; aminoglycosides; macrolides etc.

The dosage may vary within wide limits but should be adapted to the specific situation. In general the dosage given in oral form should daily be between about 3 mg and about 4 g, preferably between about 0.2 g and about 4 g, especially preferred between 0.2 g and 2 g per adult with a body weight of about 70 kg. The dosage should be administered preferably in 1 to 3 doses per day which are of equal weight. As usual children should receive lower doses which are adapted to body weight and age.

The invention also relates to a process for the manufacture of compounds of formula 1:

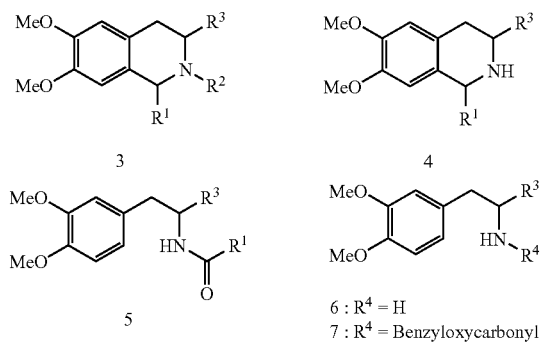

3

4

5

6 : $R^4$ = H
7 : $R^4$ = Benzyloxycarbonyl

The process consists of demethylating compounds of the structure 3 with standard reagents such as boron tribromide or hydrobromic acid. Compounds 3 in turn can be prepared by reacting a compound 4 with suitable alkylating agents $R^2X$, where $R^2$ has the meaning given in formula 1, and X is an appropriate leaving group such as chloride, bromide, iodide, methane sulfonate etc.

The structures 4 can be prepared in two ways:
From a compound of formula 5 via the Bischler-Napieralsky reaction; this method is preferred if $R^1$ is lower alkyl.
From a compound of formula 6 or 7 via the Pictet-Spengler reaction; this approach is especially useful if $R^1$ is hydrogen.

REFERENCES

R. J. Spangler et al., *J. Org. Chem.*, (1974), 36 (10), 1368-1374.
J. L. Vicario, D. Badia, E. Dominguez, L. Carrillo, *J. Org. Chem.* (1999), 64, 4610-4616
E. Dominguez, M. D. Badia, L. Castedo, D. Dominguez, *Tetrahedron*, (1988), 44, 203-208
A. Yokoyama, T. Ohwada, K. Shudo, *J. Org. Chem.* 1999, 64, 611-617

Compounds of formula 5 can be prepared by reacting a compound of formula 6 with a suitable acylating reagent like $R^1COX$, whereby $R^1$ has the meaning given in formula 1, and X is as defined above, or an anhydride like $(R^1CO)_2O$, in presence of a base (i.e. triethylamine) in an aprotic solvent, typically methylene chloride.

Compounds of formula 6 can be prepared using Leukart reductive amination conditions from a ketone of formula 8, followed by hydrolysis of the formyl group

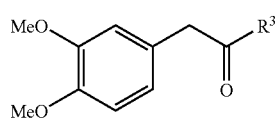

8 under strong alkalines conditions.

Compounds of formula 8 can be prepared in two ways:
I. From Friedel-Crafts reaction when $R^3$ represents —$(CH_2)_n$—$Ar^2$, —$(CH_2)_n$—$Ar^3$, or —$(CH_2)_n$—$Ar^4$, and n is equal to zero whereby $R^3$, n, $Ar^2$, $Ar^3$ and $Ar^4$ have the meaning given in formula 1. The acyl chloride of homoveratric acid reacts in presence of a Lewis acid (i.e. $AlCl_3$) with an aromatic $Ar^2$, $Ar^3$ or $Ar^4$ (Scheme I). When those aromatic rings are deactivated, or n is not equal to zero, another approach (following way II) has to be used.

Scheme I

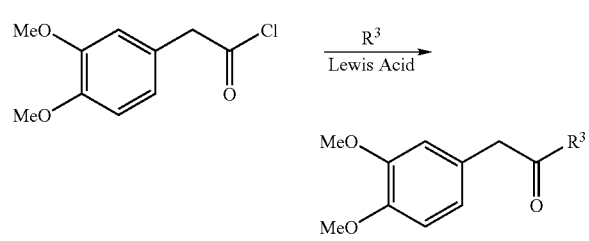

8

II. From a malonate synthetic pathway. This pathway is suitable when $R^3$ represents —$(CH_2)_n$—$Ar^2$, —$(CH_2)_n$—$Ar^3$, or —$(CH_2)_n$—$Ar^4$ and n is equal to the number 0 (deactivated aromatic ring), 1, 2 and 3 whereby $R^3$, n, $Ar^2$, $Ar^3$ and $Ar^4$ have the meaning given in formula 1.

Scheme II

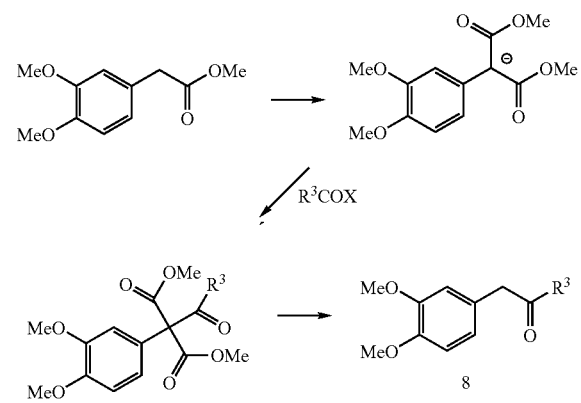

The deprotonated 3,4-dimethoxyphenylmalonate reacts with an acyl halide $R^3COX$ whereby $R^3$ has the meaning given in formula 1, and X is an appropriate leaving group such as chloride, bromide, iodide, methane sulfonate (etc.)

(Scheme II), to give the corresponding malonic ketone which can be decarboxylated under strong acidic conditions (i.e. 6N HCl in acetic acid)

REFERENCES

D. I. Kim et al., *Bioorg. Med. Chem. Lett*, (1999), 9, 85-90.
C. Cope, L. Field, D. W. H. MacDowel, M. E. Wright, *J. Amer. Chem. Soc.*, (1956), 78, 2547-2551.

When $R^3$ represents one of the groups: $-CH_2-O-(CH_2)_n-Ar^1$; $-CH_2-NH-(CH_2)_n-Ar^1$; $-CH_2-S-(CH_2)_n-Ar^1$; $-(CH=CH)-(CH_2)_n-Ar^1$; $-CHOH-(CH^2)_n-Ar^1$ whereby $R^3$, n and $Ar^1$ have the meaning given in formula 1, a parallel synthesis approach from a common "scaffold" can be developed.

The synthesis of the "scaffold" can be carried out by reacting veratraldehyde with hippuric acid (Scheme III), transesterifying the azlactone with methanol to give the compound of formula 9. Catalytic hydrogenation of the double bond followed by reduction with $LiAlH_4$ give the compound of formula 10. Pictet-Spengler cyclisation, debenzylation and protection as a carbamate (e.g. tert.-Butoxycarbonyl (BOC)) lead to the compound of formula 11.

Couplings under Mitsunobu conditions with alcohols, amines or thiols generate compounds of formula 12.

After oxidation of the primary carbinol 11 to the aldehyde, alkenes become accessible by Wittig synthesis, as well as alkanes after hydrogenation of the Wittig products. Furthermore, the aldehyde may be reacted with Grignard reagents, to yield the respective secondary alcohols of formula 12 ($R^3=-CHOH-(CH_2)_n-Ar^1$).

BOC protecting group removal is carried out concomitantly with demethylation conditions and lead in one step to compounds of structure 2.

REFERENCES

J. S. Buck, W. S. Ide, Organic Syntheses, Vol II, 55-56.
Patent specification GB1475913, IE40624, 10 October 1974 No. 2101/74: Phenylpropanolamines
E. D. Cox, J. M. Cooks, *Chem Rev.*, (1995), 95, 1797-1842.
N. J. O'Reilly, W. S. Derwin, H. C. Lin, *Synthesis*, (1990), 550-556.

Compounds of formula 7 can be prepared by α-alkylation of an ester 14 with bromide 13, followed by saponification (Scheme IV). The resulting carboxylic acid is converted in the presence of an amine and diphenylphosphoryl azide to acyl azide which undergoes a modified Curtius reaction in the presence of an alcohol to give the alkylcarbamate directly. With benzyl alcohol, the benzyloxycarbamate 7 is stable to acidic conditions required in Pictet-Spengler cyclisation.

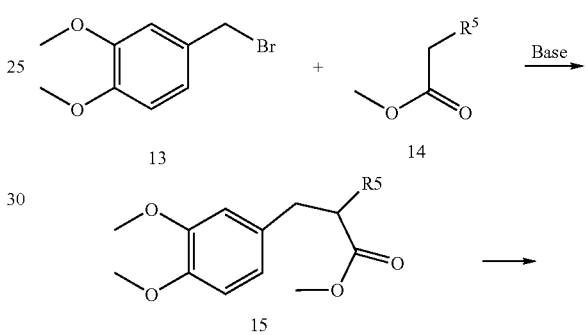

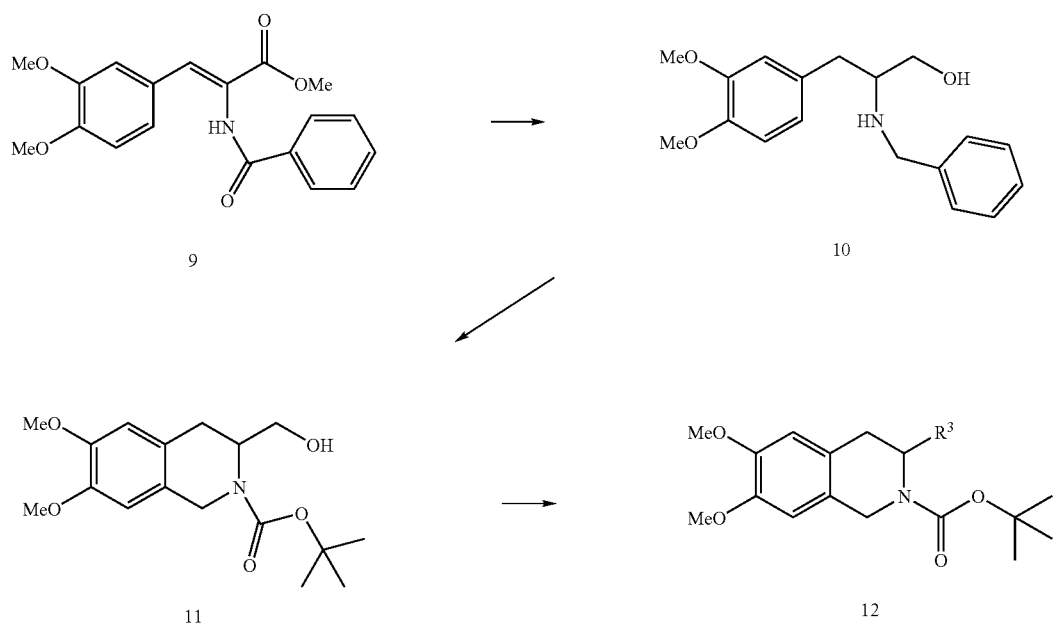

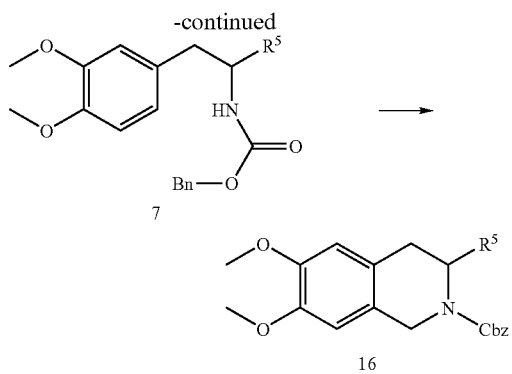

Compounds of formula 16 whereby $R^5$ represents an halogenated aryl or heteroaryl (i.e. 4-bromo phenyl 17) can be furthermore transformed into biphenyls 18 with variously substituted phenylboronic acids by means of Suzuki coupling, whereby $Ar^1$ has the meaning defined in formula 1 above (Scheme V).

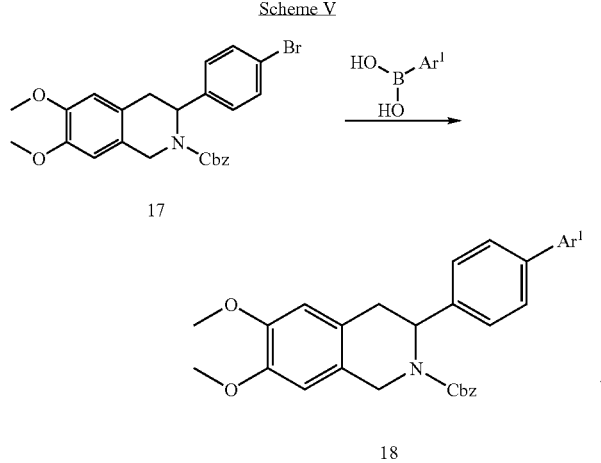

EXAMPLE

The following examples illustrate the invention but do not limit the scope thereof. All temperatures are stated in degree centigrades.

The following abbreviations are used:

BOC: tert-Butoxycarbonyl, Cbz: Benzyloxycarbonyl, DEAD: diethyl azodicarboxylate, dec.: decomposition, DMF: dimethylformamide, EtOAc: ethyl acetate, EtOH: ethanol, eq.: molar equivalents, LC/ESI-MS: Liquid chromatography coupled to electron spray ionisation mass spectrometry, mp: melting point, $^1$H NMR: proton nuclear magnetic resonance, (multiplicity: m: multiplet, s: singlet, d: doublet, dd: doublet of doublet, ddd: doublet of doublet of doublet), Pd (dppf): [1,1'-Bis(diphenylphosphino)ferrocene] dichloropalladium(II), THF:tetrahydrofuran.

The identity and purity of the compounds was examined by LC/ESI-MS. m/e values for the positive ion signals which are set forth in the Table 2 below.

TABLE 2

| Example | Scheme | molecular weight in g/mol | MS pos mode m/e in u |
|---|---|---|---|
| 1 | I | 333.1 | 334.0 |
| 2 | I | 423.2 | 424.1 |
| 3 | I | 347.15 | 348.0 |
| 4 | I | 321.1 | 322.0 |
| 5 | I | 307.1 | 308.0 |
| 6 | III | 195.1 | 196.1 |
| 7 | I | 331.1 | 331.9 |
| 8 | I | 349.1 | 349.9 |
| 9 | I | 309.0 | 310.0 |
| 10 | III | 339.0 | 340.1 |
| 11 | III | 429.1 | 430.1 |
| 12 | I | 290.1 | 290.9 |
| 13 | III | 339.04 | 340.1 |
| 14 | III | 339.04 | 340.1 |
| 15 | IV | 275.07 | 276.4 |
| 16 | IV | 319.02 | 320.3 |
| 17 | V | 385.13 | 386.0 |
| 18 | V | 360.18 | 360.9 |
| 19 | V | 333.14 | 333.9 |
| 20 | V | 333.14 | 334.0 |
| 21 | V | 353.12 | 353.9 |
| 22 | V | 342.14 | 343.0 |

Example 1

3-(4-Phenoxy-phenyl)-1,2,3,4-tetrahydro-isoquinoline-6,7-diol

Step A: Homoveratric acid (20 mmol) was converted to the acyl chloride by 4.5 hours reflux in toluene (200 ml) with $SOCl_2$ (2.3 eq). Cooled and evaporated to dryness. Reacted under Friedel-Crafts conditions in $CH_2Cl_2$ (100 ml) with diphenyl ether (1.1 eq) using $AlCl_3$ (2.2 eq) as Lewis acid at −20° C. for 4 hours yielding the corresponding deoxybenzoin as solid in 85% yield after recrystallisation from EtOAc, mp 111-112° C.

$^1$H NMR (CDCl$_3$): 8.05-7.95 (m, 2H), 7.55-7.45 (m, 2H), 7.2 (m, 1H), 7.1-7.05 (m, 2H), 7.0-6.95 (m, 2H), 6.85-6.75 (m, 2H), 4.17 (s, 2H), 3.85 (s, 6H).

Step B: Leuckart reductive amination of the ketone (2.0 g, 1 eq.) with formamide (10 eq.) in ammonium formate (20 eq.) in 90% formic acid (10 eq.) at 190° C. for 6 hours gave 1.8 g of crystalline formylated amine in 83% yield, mp 138-139° C. (dec.). Hydrolysis in NaOH 4N-EtOH (1:5 v/v) at reflux for 5 hours generated the 1,2-diarlethylamine in 95% yields.

Step C: Standard Pictet-Spengler cyclisation of the primary amine (0.3 g, 0.86 mmol) with aqueous formaldehyde (0.43 ml, 6 eq.) in HCl 1N (30 ml) and THF (3 ml) and stirring for 18 hours at 70° C. followed by alkaline work-up, gave the product in virtually quantitative yield (0.34 g, 99%).

Step D: The derivative (0.29 g, 0.8 mmol) stirred in dry $CH_2Cl_2$ (8 ml) was demethylated by addition of $BBr_3$ 1M solution in $CH_2Cl_2$ (2 eq.) at 0° C. under Ar for 16 hours. Addition of dry methanol (0.5 ml) followed by evaporation (repeated twice) and trituration in dry ether afforded the expected product (0.26 g, 80%) as the hydrobromide salt.

Example 2

2-Benzyl-3-(4-phenoxy-phenyl)-1,2,3,4-tetrahydro-isoquinoline-6,7-diol

Compound obtained in example 1, step C (0.1 g, 0.277 mmol) stirred in dry DMF (1.2 ml) was treated with potassium carbonate (3 eq), and benzyl bromide (1.5 eq) at 20° C. for 16 hours. The product was extracted in EtOAc, washed with water, brine, dried, evaporated to an oil that was purified on silia gel, eluted with EtOAc-hexanes (1:4), gave 0.1 g (82%) of product.

Rf Ether-hexanes (1:1)=0.54.

Demethylation according to conditions described in example 1 gave the title compound as the hydrobromide salt (117 mg, 87%)

Example 3

1-Methyl-3-4-phenoxy-phenyl)-1,2,3,4-tetrahydro-isoquinoline-6,7-diol

Primary amine from example 1 (200 mg) was reacted with acetyl chloride (1.3 eq.) in dry ethylamine (3 eq.) and dry dichloromethane (5 ml) at 0° C. for 1 hour, then 25° C. for 14 hours and gave the acetamide in 88% yield. The acetamide (103 mg, 0.263 mmol) was refluxed for 3 hours with $POCl_3$ (7.5 eq.) in dry toluene (10 ml) at 110° C. for 14 hours followed by $NaBH_4$ reduction (11 eq.) in dry ethanol gave the corresponding 1,2,3,4-tetrahydroisoquinoline (50 mg, 51%). Demethylation as in example 1 gave the expected product as the hydrobromide salt (50 mg, 87%).

Example 4

3-(4-Methoxy-naphthalen-1-yl)-1,2,3,4-tetrahydro-isoquinoline-6,7-diol:

1-Methoxynaphtalene ether was coupled under Friedel-Crafts conditions as described in example 1, step A. The ketone was obtained in 82% yield after recrystallisation from EtOAc, mp 127-128° C.

$^1$H NMR ($CDCl_3$): 8.88 (d, 1H, J=8.5 Hz), 8.30 (dd, 1H, J=7.6 and 1.5 Hz), 8.05 (d, 1H, J=8.0 Hz), 7.58 (ddd, 1H, J=8.1, 6.6, 1.5 Hz), 7.51 (ddd, 1H, J=8.1, 7.1, 1.5 Hz), 6.85 (s, 1H), 6.82 (dd, 1H, J=4.0, 2.0 Hz), 6.81 (s, 1H), 6.77 (d, 1H, J=8.0 Hz), 4.29 (s, 2H), 4.0 (s, 3H), 3.84 (s, 6H).

Reductive amination was performed as described in example 1, step B (46%) (formylated amine: mp 198-201° C. (dec.)), followed by cyclisation, step C (94%), and demethylation, step D gave, after trituration in dry ether, the title compound as a hydrobromide salt.

Example 5

3-(4-Hydroxy-naphthalen-1-yl)-1,2,3,4-tetrahydro-isoquinoline-6,7-diol:

Same procedure as in example 4. Demethylation required 5 eq. of $BBr_3$ to demethylate the methoxy of naphthalene.

Example 6

3-Hydroxymethyl-1,2,3,4-tetrahydro-isoquinoline-6,7-diol:

Veratraldehyde was reacted with hippuric acic to give the azlactone which was then reacted with sodium methoxide in methanol at 25° C. (see: J. S. Buck, W. S. Ide, Organic Syntheses, Vol II, 55-56.). The azlactone (20 g) was hydrogenated under hydrogen atmosphere (1 atm., 3 l) on Pd/C (10%, 1.0 g) in methanol (1.0 l) at 25° C. for 16 hours, giving 19.24 g (96%) of product as a solid (mp 96-97° C. (from EtOAc-hexanes)), ESI-MS=344.0 (M+1). The ester and amide groups of intermediate (11.51 g, 33.5 mmol) were reduced with lithium aluminium hydride (3 eq.) in dry THF (250 ml) at reflux for 15 hours to yield after aqueous work-up, 2-benzylamino-3-(3,4-dimethoxy-phenyl)-propan-1-ol in virtually quantitative yield (10.0 g) as a white solid (mp 114-116° C.), ESI-MS=302.1 (M+1). Standard Pictet-Spengler cyclisation of benzylamine derivative (3.0 g, 1 eq.) employing aqueous formaldehyde (5 eq.) in a mixture 1 N HCl (170 ml) and THF (25 ml) upon stirring for 12 hours at 60° C. afforded (2-Benzyl-6,7-dimethoxy-1,2,3,4-tetrahydro-isoquinolin-3-yl)-methanol in virtually quantitative yields (3.1 g) as an oil. $^1$H NMR ($CDCl_3$): 7.6-7.3 (m, 5H), 6.65 (s, 1H), 6.49 (s, 1H), 4.1-3.7 (m, 13H), 3.41 (large s, 1H, H3), 2.93 (dd, 1H, J=12 and 4.5 Hz), 2.61 (d, 1H, J=12 Hz), ESI-MS=314.2 (M+1).

Debenzylation of former compound (10 g) using Pd/C (10%) (800 mg) and formic acid (20 ml) in methanol (500 ml) gave the secondary amine (7.15 g, 83%) as the formate salt, ESI-MS=224.1 (M+1). Demethylation was similar to example 1, step D.

Example 7

3-Dibenzofuran-2-yl-1,2,3,4-tetrahydro-isoquinoline-6,7-diol:

Dibenzofuran was coupled under Friedel-Crafts conditions as described in example 1, step A. Ketone was obtained in 82% yield after recrystallisation from EtOAc, mp 129-130° C.

$^1$H NMR ($CDCl_3$): 8.65 (d, 1H, J=2.0 Hz), 8.16 (dd, 1H, J=9.1 and 2.0 Hz), 8.0 (d, 1H, J=7.1 Hz), 7.61 (s, 1H), 7.58 (s, 1H), 7.50 (ddd, 1H, J=8.6, 7.1, 1.0 Hz), 7.40 (ddd, 1H, J=8.6, 7.6, 1.0 Hz), 6.9-6.8 (m, 3H), 4.34 (s, 2H), 3.87 (s, 3H), 3.86 (s, 3H).

Reductive amination was performed as described in step B (53%) (formylated amine: mp 182-183° C. (dec.)), followed by cyclisation (step C, 54%) and demethylation (Step D, 61%) gave, after trituration in dry ether, the title compound as a hydrobromide salt.

Example 8

3-(4-Phenylsulfanyl-phenyl)-1,2,3,4-tetrahydro-isoquinoline-6,7-diol:

Phenyl sulfide was coupled under Friedel-Crafts conditions as described in example 1, step A. Ketone was obtained in 78% yield after recrystallisation from EtOAc, mp 69-70° C. (dec.).

$^1$H NMR ($CDCl_3$): 7.86 (d, 2H, J=8.6 Hz), 7.5-7.45 (m, 2H), 7.45-7.35 (m, 3H), 7.20 (d, 2H, J=8.6 Hz), 6.85-6.75 (m, 3H), 4.15 (s, 2H), 3.85 (s, 6H).

Reductive amination was performed as described in step B (56%) (formylated amine: mp 151-152° C. (dec.)), followed by cyclisation (step C, 91%) and demethylation (step D, 70%) gave, after trituration in dry ether, the title compound as a hydrobromide salt.

Example 9

3-(2,4-Dichloro-phenyl)-1,2,3,4-tetrahydro-isoquinoline-6,7-diol:

Homoveratric acid was esterified with concentrated sulfuric acid in methanol at reflux. The methyl ester (9 g) was coupled with dimethyl oxalate (1.1 eq) and thermally rearranged to dimethyl 3,4-dimethoxyphenylmalonate (6.22 g, 54%). Deprotonation of the malonic carbon (0.63 g) with sodium hydride (1.2 eq) in dry THF (20 ml) followed by coupling with 2,4-dichlorobenzoyl chloride (1.3 eq) at room temperature for 16 hours gave the corresponding malonic ketone that was crystallized in methanol (0.91 g, 88%, mp 118-120° C.), $^1$H NMR (CDCl$_3$): 7.41 (d, 1H, J=2.2 Hz), 7.1-7.0 (m, 2H), 6.94 (d, 1H, J=2.5 Hz), 6.92 (d, 1H, J=2.0 Hz), 6.83 (d, 1H, J=8.6 Hz), 6.73 (d, 1H, J=8.6 Hz), 3.89 (s, 3H), 3.83 (s, 9H).

Decarboxylation under drastic acidic conditions (HCl 6N in acetic acid) at 100° C. for 5 hours gave, after column chromatography on silica gel (EtOAc-hexanes (1:9)) the expected ketone (43%).

$^1$H NMR (CDCl$_3$): 7.41 (d, 1H, J=2.2 Hz), 7.32 (d, 1H, J=8.1 Hz), 7.25 (dd, 1H, J=8.6 and 2.1 Hz), 6.85-6.75 (m, 3H), 4.16 (s, 2H), 3.85, 3.84 (2 s, 6H).

The subsequent steps, i.e amination, cyclisation and demethylation, are similar to example 1.

Example 10

3-(2,4-Dichloro-phenoxymethyl)-1,2,3,4-tetrahydro-isoquinoline-6,7-diol:

Step A: the secondary amine of the derivative synthesized in example 6 (2 g, ESI-MS=224.1 (M+1)) was protected with di-tert. butyl dicarbonate (2 eq) in CH$_2$Cl$_2$ (60 ml) in presence of triethylamine (4 eq.) at 20° C. for 16 hours to finally afford a key intermediate ("scaffold") (2.2 g, 92%) as a white solid. mp 137-139° C. $^1$H NMR (CDCl$_3$): 6.63 (s, 1H), 6.61 (s, 1H), 4.8-4.1 (2 m, 3H), 3.86 (s, 6H), 3.51 (large s, 2H), 2.98 (dd, 1H, J=15.7 and 6.1 Hz), 2.69 (d, 1H, J=14.8 Hz), 1.51 (s, 9H); ESI-MS=323.8 (M+1).

Step B: to the scaffold (0.31 mmol), triphenylphosphine (1.3 eq.) and 2,4-dichlorophenol (1 eq.) stirred in dry THF (4 ml) at 25° C. under argon, diethyl azodicarboxylate (1.3 eq.) was added dropwise. After 2,5 hours, the reaction mixture was evaporated to dryness. Purification by flash chromatography yielded 77 mg (54%) of the desired product.

Step C: demethylation conditions identical to example 1 simultaneously removed the BOC protecting group and afforded the final product as the hydrobromide salt in 55% yield.

Example 11

2-Benzyl-3-(2,4-dichloro-phenoxymethyl)-1,2,3,4-tetrahydro-isoquinoline-6,7-diol:

The synthesis is identical to example 10, followed by the N-alkylation procedure described in example 2.

Demethylation was similar to example 1, step D.

Example 12

3-Biphenyl-4-yl-1,2,3,4-tetrahydro-isoquinoline-6,7-diol:

Biphenyl was coupled under Friedel-Crafts conditions as described in example 1, step A. Ketone was obtained in 89% yield after recrystallisation from EtOAc, mp 107-108° C.

$^1$H NMR (CDCl$_3$): 8.09 (d, 2H, J=8.6 Hz), 7.67 (d, 2H, J=8.6 Hz), 7.60 (d, 2H, J=6.6 Hz), 7.47 (t, 2H, J=7.6 Hz), 7.41 (d, 1H, J=7.6 Hz), 6.9-6.8 (m, 3H), 4.25 (s, 2H), 3.87 (s, 3H), 3.86 (s, 3H).

Reductive amination was performed as described in step B (64%) (formylated amine: mp 168-169° C. (dec.)), followed by cyclisation (step C, 45%) and demethylation (Step D, 74%). Trituration in dry ether gave the title compound as a hydrobromide salt.

Example 13

3-(3,4-Dichloro-phenoxymethyl)-1,2,3,4-tetrahydro-isoquinoline-6,7-diol:

The synthesis is identical to example 10. Only in step B, 3,4-dichlorophenol was used.

Example 14

3-(2,5-Dichloro-phenoxymethyl)-1,2,3,4-tetrahydro-isoquinoline-6,7-diol:

The synthesis is identical to example 10. Only in step B, 2,5-dichlorophenol was used.

Example 15

3-(4-Chloro-phenyl)-1,2,3,4-tetrahydro-isoquinoline-6,7-diol:

Step A: lithium diisopropylamide (1.1 eq, 2 M solution in THF) was slowly added to (4-Chloro-phenyl)-acetic acid methyl ester (2 g) stirred in dry THF (30 ml) at −78° C. After 30 minutes, 4-Bromomethyl-1,2-dimethoxy-benzene (1 eq) in THF (10 ml) was slowly added. The reaction mixture was heated to 20° C. and stirred for an additional hour. Poured in water and extracted with ethyl acetate. Solid extraction on silica gel gave 2.94 g of product (81%).

Step B: saponification of ester (2.4 g) with NaOH 2 M (2 eq) in methanol (40 ml) at reflux for 2 hours generated the acid quantitatively.

Step C: triethylamine (1.1 eq), benzyl alcohol (3 eq) and diphenylphosphoryl azide (1.1 eq) were successively added to acid (1 g) stirred in dry THF (50 ml) under Argon at 20° C. The mixture was refluxed for 16 hours. Purification on silica gel provided 0.91 g (68%) of expected product.

Step D: Pictet-Spengler cyclisation of the carbamate 7 (1.2 g) was performed in formic acid (35 ml) and formaldehyde 36% (2.2 ml) at 70° C. for 5 hours, affording 0.7 g (56%) of the corresponding tetrahydroisoquinoline.

Demethylation conditions identical to example 1 simultaneously removed the Cbz protecting group and afforded the final product as the hydrobromide salt in 51% yield.

Example 16

3-(4-Bromo-phenyl)-1,2,3,4-tetrahydro-isoquinoline-6,7-diol:

Same conditions as example 15 with (4-Bromo-phenyly-acetic acid methyl ester as starting material.

Example 17

3-(4'-Trifluoromethyl-biphenyl-4-yl)-1,2,3,4-tetrahydro-isoquinoline-6,7-diol:

To bromo derivative 17 (0.2 mmol) and 4-trifluoromethylphenylboronic acid (1.2 eq) were solubilized in dioxane (4 ml) under Argon, added Pd(dppf) (0.04 eq) followed by a 2 M potassium carbonate solution (0.25 ml). Stirred at 110° C. for 14 hours. Extraction with EtOAc and bicarbonate washing gave an oil that was purified on silica gel. Product (43 mg, 38%) was collected.

Cbz hydrolysis and demethylation were performed in one step in HBr 30% in acetic acid solution at 100° C. for 16 hours (61%).

Example 18

3-(4'-Dimethylamino-biphenyl-4-yl)-1,2,3,4-tetrahydro-isoquinoline-6,7-diol:

The synthesis is identical to example 17 with 4-dimethylaminophenylboronic acid used instead.

Example 19

3-(4'-Hydroxy-biphenyl-4-yl)-1,2,3,4-tetrahydro-isoquinoline-6,7-diol:

The synthesis is identical to example 17 with 4-methoxyphenylboronic acid used instead (32%).

Demethylation conditions identical to example 1 simultaneously removed the Cbz protecting group and afforded the final product as the hydrobromide salt in 74% yield.

Example 20

3-(2'-Hydroxy-biphenyl-4-yl)-1,2,3,4-tetrahydro-isoquinoline-6,7-diol:

The synthesis is identical to example 17 with 2-methoxyphenylboronic acid used instead (37%).

Demethylation conditions were identical to example 19 (89%).

Example 21

3-(2',4'-Difluoro-biphenyl-4-yl)-1,2,3,4-tetrahydro-isoquinoline-6,7-diol:

The synthesis is identical to example 17 with 2,4-difluorophenylboronic acid used instead (47%).

Demethylation conditions were identical to example 19 (65%).

Example 22

4'-(6,7-Dihydroxy-1,2,3,4-tetrahydro-isoquinolin-3-yl)-biphenyl-3-carbonitrile

The synthesis is identical to example 17 with 3-cyanophenylboronic acid used instead (68%).

Demethylation conditions were identical to example 19 (95%).

The invention claimed is:

1. A compound of formula 1 wherein
$R^1$ represents hydrogen or lower alkyl,
$R^2$ represents hydrogen; aryl; aryl-lower alkyl; heteroaryl; or heteroaryl-lower alkyl;
wherein the aryl and heteroaryl residues may be mono-, di- or tri-substituted with lower alkyl, hydroxy, lower alkoxy, halogen, trifluoromethyl, amino, lower alkylamino, or lower alkylendioxy, and which substituents may be the same or different,
$R^3$ represents one of the groups: $—(CH_2)_m—O—(CH_2)n-Ar^1$; $—(CH_2)_m—NH—(CH_2)_n—Ar^1$; $—(CH_2)_m—S—(CH_2)_n—Ar^1$; $—(CH=CH)—(CH_2)_n—Ar^1$; $—CHOH—(CH_2)_n—Ar^1$; $—(CH_2)_n—Ar^2$; $—CH_2—Ar^{2'}$; $—(CH_2)n-Ar^3$; and $—(CH_2)_n—Ar^4$, wherein
m represents the number 1, 2 or 3;
n represents the number 0, 1, 2 or 3; and
in case $Ar^2$ is present, n has the meaning 0, 2 or 3;
$Ar^1$ represents hydrogen; an aryl or heteroaryl group, which group may be unsubstituted or mono-, di-, or trisubstituted with a substituent independently selected from the group D, wherein D represents hydroxy, lower alkyl, lower alkoxy, lower alkylendioxy, aryl, aryloxy, lower alkyl-sulfanyl, arylsulfanyl, halogen, amino, lower alkylamino, lower di-alkylamino, or trifluoromethyl;
$Ar^2$ represents an aryl or heteroaryl group, which group is di-, or trisubstituted with a substituent selected from the group D, wherein D is as defined above;
$Ar^{2'}$ represents an aryl or heteroaryl group, which group is di-, or trisubstituted with, lower alkyl, lower alkylendioxy, aryl, aryloxy, lower alkyl-sulfanyl, arylsulfanyl, halogen, amino, lower alkylamino, lower di-alkylamino, or trifluoromethyl;
$Ar^3$ represents an aryl or heteroaryl group, which group is monosubstituted with aryl, aryloxy, arylsulfanyl, lower alkyl-sulfanyl, trifluoromethyl, or lower alkylendioxy;
$Ar^4$ represents an aryl or heteroaryl group, which group is monosubstituted with $Ar^1$ with the proviso that $Ar^1$ does not represent hydrogen, or a pure enantiomer, a mixture of enantiomers, a pure diastereomer, a mixture of diastereomers, diastereomeric racemates and stereoisomers, or a pharmaceutically acceptable salt thereof.

2. A compound of formula 2 wherein
R¹ represents hydrogen or lower alkyl, and
R³ represents one of the groups: —(CH$_2$)$_m$—O—(CH$_2$)$_n$—Ar¹; —(CH$_2$)$_m$—NH—(CH$_2$)$_n$—Ar¹; —(CH$_2$)$_m$—S—(CH$_2$)$_n$—Ar¹; —(CH=CH)—(CH$_2$)$_n$—Ar¹; —CHOH—(CH$_2$)$_n$—Ar¹; —(CH$_2$)$_n$—Ar²; —CH$_2$—Ar²'; —(CH$_2$)$_n$—Ar³; and —(CH$_2$)$_n$—Ar⁴,
wherein
  m represents the number 1, 2 or 3;
  n represents the number 0, 1, 2 or 3; and
  in case Ar² is present, n has the meaning 0, 2 or 3;
  Ar¹ represents hydrogen; an aryl or heteroaryl group, which group may be unsubstituted or mono-, di-, or trisubstituted with a substituent independently selected from the group D, wherein D represents hydroxy, lower alkyl, lower alkoxy, lower alkylendioxy, aryl, aryloxy, lower alkyl-sulfanyl, arylsulfanyl, halogen, amino, lower alkylamino, lower di-alkylamino, or trifluoromethyl;
  Ar² represents an aryl or heteroaryl group, which group is di-, or trisubstituted with a substituent selected from the group D, wherein D is as defined above;
  Ar²' represents an aryl or heteroaryl group, which group is di-, or trisubstituted with, lower alkyl, lower alkylendioxy, aryl, aryloxy, lower alkyl-sulfanyl, arylsulfanyl, halogen, amino, lower alkylamino, lower di-alkylamino, or trifluoromethyl;
  Ar³ represents an aryl or heteroaryl group, which group is monosubstituted with aryl, aryloxy, arylsulfanyl, lower alkyl-sulfanyl, trifluoromethyl, or lower alkylendioxy;
  Ar⁴ represents an aryl or heteroaryl group, which group is monosubstituted with Ar¹ with the proviso that Ar¹ does not represent hydrogen, or a pure enantiomer, a mixture of enantiomers, a pure diastereomer, a mixture of diastereomers, diastereomeric racemates and stereoisomers, or a pharmaceutically acceptable salt thereof.

3. The compound of claim 1, wherein R¹ represents hydrogen.

4. A compound selected from the group consisting of:
3-(4-Phenoxy-phenyl)-1,2,3,4-tetrahydro-isoquinoline-6,7-diol;
2-Benzyl-3-(4-phenoxy-phenyl)-1,2,3,4-tetrahydro-isoquinoline-6,7-diol;
1-Methyl-3-(4-phenoxy-phenyl)-1,2,3,4-tetrahydro-isoquinoline-6,7-diol;
3-(4-Methoxy-naphthalen-1-yl)-1,2,3,4-tetrahydro-isoquinoline-6,7-diol;
3-(4-Hydroxy-naphthalen-1-yl)-1,2,3,4-tetrahydro-isoquinoline-6,7-diol;
3-Hydroxymethyl-1,2,3,4-tetrahydro-isoquinoline-6,7-diol;
3-Dibenzofuran-2-yl-1,2,3,4-tetrahydro-isoquinoline-6,7-diol;
3-(4-Phenylsulfanyl-phenyl)-1,2,3,4-tetrahydro-isoquinoline-6,7-diol;
3-(2,4-Dichloro-phenyl)-1,2,3,4-tetrahydro-isoquinoline-6,7-diol;
3-(2,4-Dichloro-phenoxymethyl)-1,2,3,4-tetrahydro-isoquinoline-6,7-diol;
2-Benzyl-3-(2,4-dichloro-phenoxymethyl)-1,2,3,4-tetrahydro-isoquinoline-6,7-diol;
3-Biphenyl-4-yl-1,2,3,4-tetrahydro-isoquinoline-6,7-diol;
3-(3,4-Dichloro-phenoxymethyl)-1,2,3,4-tetrahydro-isoquinoline-6,7-diol;
3-(2,5-Dichloro-phenoxymethyl)-1,2,3,4-tetrahydro-isoquinoline-6,7-diol;
3-(4-Chloro-phenyl)-1,2,3,4-tetrahydro-isoquinoline-6,7-diol;
3-(4-Bromo-phenyl)-1, 2,3,4-tetrahydro-isoquinoline-6,7-diol;
3-(4'-Trifluoromethyl-biphenyl-4-yl)-1,2,3,4-tetrahydro-isoquinoline-6,7-diol;
3-(4'-Dimethylamino-biphenyl-4-yl)-1,2,3,4-tetrahydro-isoquinoline-6,7-diol;
3-(4'-Hydroxy-biphenyl-4-yl)-1,2,3,4-tetrahydro-isoquinoline-6,7-diol;
3-(2'-Hydroxy-biphenyl-4-yl)-1,2,3,4-tetrahydro-isoquinoline-6,7-diol;
3-(2',4'-Difluoro-biphenyl-4-yl)-1,2,3,4-tetrahydro-isoquinoline-6,7-diol; and
4'-(6,7-Dihydroxy-1,2,3,4-tetrahydro-isoquinolin-3-yl)-biphenyl-3-carbonitrile.

5. A pharmaceutical composition comprising a compound of any one of claims 1-3 or 4 and a pharmaceutically acceptable carrier and/or an adjuvant.

6. A process for the manufacture of a pharmaceutical composition, comprising one or more compounds as claimed in any one of claims 1-3 or 4 as active ingredients, which process comprises mixing one or more active ingredients with a pharmaceutically acceptable excipient.

7. A method of treating a bacterial infection, comprising administering a therapeutically effective amount of the compound of any one of claims 1-3 or 4.

8. The method of claim 7, wherein the infection is caused by a Gram positive pathogen and/or a Gram negative pathogen.

9. A method of treating a bacterial infection, comprising administering a therapeutically effective amount of the pharmaceutical composition of claim 5.

10. The method of claim 9, wherein the infection is caused by a Gram positive pathogen and/or a Gram negative pathogen.

* * * * *